United States Patent
Kano et al.

(10) Patent No.: US 10,368,736 B2
(45) Date of Patent: Aug. 6, 2019

(54) OCT MOTION CONTRAST DATA ANALYSIS APPARATUS AND OCT MOTION CONTRAST DATA ANALYSIS METHOD

(71) Applicant: NIDEK CO., LTD., Gamagori, Aichi (JP)

(72) Inventors: Tetsuya Kano, Aichi (JP); Ryosuke Shiba, Aichi (JP); Kazuki Okada, Aichi (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 129 days.

(21) Appl. No.: 15/255,461

(22) Filed: Sep. 2, 2016

(65) Prior Publication Data
US 2017/0069105 A1 Mar. 9, 2017

(30) Foreign Application Priority Data
Sep. 4, 2015 (JP) ................. 2015-175194

(51) Int. Cl.
| | | |
|---|---|---|
| *G06K 9/00* | (2006.01) | |
| *A61B 3/00* | (2006.01) | |
| *A61B 3/10* | (2006.01) | |
| *G06T 7/11* | (2017.01) | |
| *G06T 7/136* | (2017.01) | |

(52) U.S. Cl.
CPC ............ *A61B 3/0091* (2013.01); *A61B 3/102* (2013.01); *A61B 3/1025* (2013.01); *G06T 7/11* (2017.01); *G06T 7/136* (2017.01); *G06T 2207/10101* (2013.01); *G06T 2207/20092* (2013.01); *G06T 2207/30041* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 2013/0301008 A1 | 11/2013 | Srivastava et al. | |
| 2014/0205169 A1* | 7/2014 | Yamakawa | ........... G06T 7/0012 382/131 |

(Continued)

FOREIGN PATENT DOCUMENTS

| | | |
|---|---|---|
| JP | 2014-217423 A | 11/2014 |
| JP | 2015-515894 A | 6/2015 |

OTHER PUBLICATIONS

Roberto Reif et al: "Quantifying Optical Microangiography Images Obtained from a Spectral Domain Optical Coherence Tomography System" Hindawi Publishing Corporation, International Journal of Biomedical Imaging, vol. 2012, Article ID 509783, Apr. 13, 2012, pp. 1-11 (12 pages total).

(Continued)

*Primary Examiner* — Atiba O Fitzpatrick
(74) *Attorney, Agent, or Firm* — Sughrue Mion, PLLC

(57) ABSTRACT

An OCT motion contrast data analysis apparatus includes: a processor; and memory storing computer readable instructions, when executed by the processor, causing the OCT motion contrast data analysis apparatus to execute: acquiring OCT motion contrast data of a subject by an optical coherence tomography; and performing an analysis process with respect to the OCT motion contrast data based on an analysis chart set on image data different from the OCT motion contrast data.

18 Claims, 4 Drawing Sheets

(56) References Cited

U.S. PATENT DOCUMENTS

2014/0327916 A1    11/2014   Inoue
2015/0168127 A1*   6/2015   Takeno .............. G01B 9/02091
                                                                                       356/479
2016/0317029 A1    11/2016   Srivastava et al.

OTHER PUBLICATIONS

Communication dated Jun. 4, 2019, from the Japanese Patent Office in counterpart application No. 2015-175194.
Communication dated May 14, 2019, from the Japanese Patent Office in counterpart application No. 2015-175194.
Yali Jia et al. "Quantitative OCT angiography of optic nerve head blood flow" Biomedical optics Express, vol. 3, No. 12, Nov. 7, 2012 (11 pages total).

* cited by examiner

OCT MOTION CONTRAST DATA ANALYSIS APPARATUS AND OCT MOTION CONTRAST DATA ANALYSIS METHOD

CROSS REFERENCE TO RELATED APPLICATION

This application is based upon and claims the benefit of priority of Japanese Patent Application No. 2015-175194 filed on Sep. 4, 2015, the contents of which are incorporated herein by reference in its entirety.

BACKGROUND

The present disclosure relates to an apparatus and a method for analyzing motion contrast data acquired by optical coherence tomography (OCT).

Recently, a technology obtaining motion contrast data of a subject using an OCT technology has been attracting attention (refer to Non Patent Document 1).

[Non Patent Document 1] Roberto Reif et al. "Quantifying Optical Microangiography Images Obtained from a Spectral Domain Optical Coherence Tomography System", International Journal of Biomedical Imaging, Vol. 2012, Article ID 509783, p. 11

SUMMARY

However, although various improvements are performed in order to realize imaging of the motion contrast data, there is room for improvement in an analysis relationship in various aspects.

For example, an analysis using the motion contrast data is independent of an analysis (for example, analysis of layer thickness of fundus) using OCT data, and requires a lot of effort. In addition, each analysis result is not easily compared with each of the others. A case of analyzing a plurality of the motion contrast data items requires a lot of effort.

This disclosure focuses on at least one of problems of the related art, and is for providing an OCT motion contrast data analysis apparatus and an OCT motion contrast data analysis method which are capable of appropriately analyzing the motion contrast data.

In order to solve the above described problems, the disclosure is characterized by having configurations as follows:

An OCT motion contrast data analysis apparatus comprising:

a processor; and memory storing computer readable instructions, when executed by the processor, causing the OCT motion contrast data analysis apparatus to execute:

acquiring OCT motion contrast data of a subject by an optical coherence tomography; and performing an analysis process with respect to the OCT motion contrast data based on an analysis chart set on image data different from the OCT motion contrast data.

An OCT motion contrast data analysis apparatus comprising:

a processor; and memory storing computer readable instructions, when executed by the processor, causing the OCT motion contrast data analysis apparatus to execute:

acquiring OCT motion contrast data of a fundus of a subject's eye by an optical coherence tomography;

setting a first analysis region to OCT data of the fundus of the subject's eye, the first analysis region being divided into a plurality of sections, and the OCT data being different from the OCT motion contrast data;

acquiring basic statistical amounts in relation to a layer thickness of the fundus in the subject's eye in each of the plurality of sections of the first analysis region;

setting a second analysis region to the OCT motion contrast data, the second analysis region being divided into a plurality of sections, an arranged position and a range of the plurality of sections of the second analysis region with respect to the OCT motion contrast data corresponding to an arranged position and a range of the plurality of sections of the first analysis region with respect to the OCT data; and analyzing the OCT motion contrast data.

An OCT motion contrast data analysis method comprising:

acquiring OCT motion contrast data of a subject by an optical coherence tomography; and performing an analysis process with respect to the OCT motion contrast data based on an analysis chart set on image data different from the OCT motion contrast data.

DESCRIPTION OF ILLUSTRATIVE EMBODIMENTS

Figure 1:
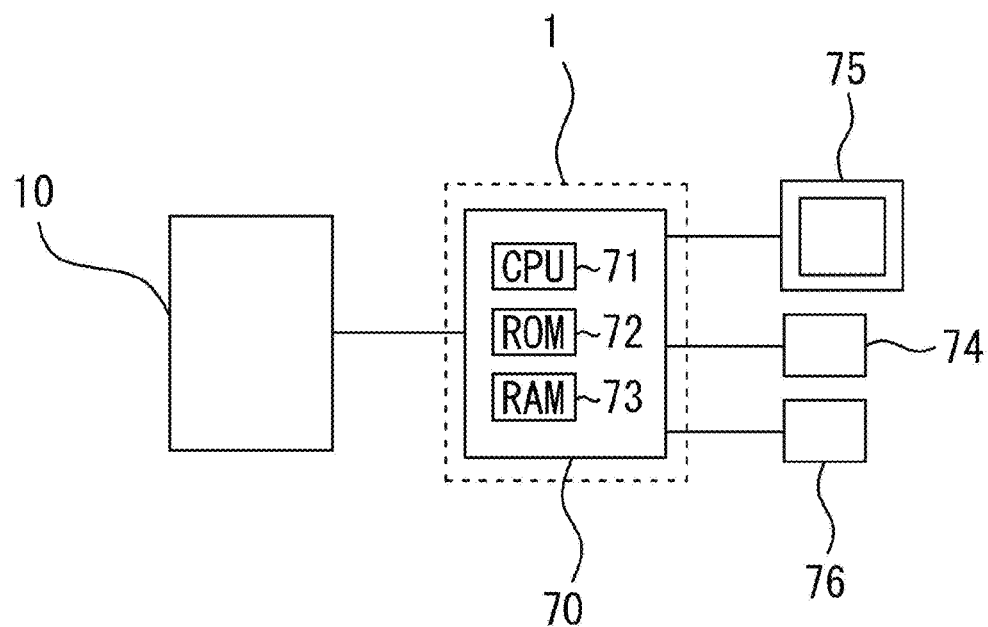
FIG. 1 is a block diagram illustrating an outline of an example.

Hereinafter, an embodiment will be simply described. An OCT motion contrast data analysis apparatus of the embodiment analyzes, for example, motion contrast data of a subject acquired by an optical coherence tomography. The OCT motion contrast data analysis apparatus is provided with, for example, an analysis processing unit (for example, controller 70). The analysis processing unit performs an analysis process with respect to the motion contrast data, for example, based on an analysis chart set on the image data. Here, the image data is different from, for example, the motion contrast data. Accordingly, the analysis apparatus is capable of smoothly performing analysis of motion contrast.

For example, the analysis processing unit may set an analysis region with respect to the motion contrast data based on a positional information of the analysis chart. The analysis processing unit may perform the analysis process with respect to the motion contrast in relation to the set analysis region. Such an analysis process may be applied for, for example, the extraction process of a blood vessel region in the analysis region.

In addition, the analysis processing unit sets a reference position at the time of performing the analysis process with respect to the motion contrast data based on the positional information of the analysis chart, and may perform the analysis process with respect to the motion contrast based on the set reference position. In this case, the analysis region may be set based on the set reference position. The analysis processing unit may perform the analysis process with respect to the motion contrast in relation to the set analysis region. Such a process may be applied to, for example, an extraction process of the blood vessel region in the analysis region. In addition, the analysis process with respect to the motion contrast data may be performed based on the set reference position. Such a process may be applied to, for example, set to a reference position at the time of performing an extraction process of a non-blood vessel region.

In addition, based on a range of the analysis chart, the analysis region in the motion contrast data may be set.

The motion contrast data may be, for example, two-dimensional motion contrast data, en face motion contrast data, and three-dimensional motion contrast data.

The analysis chart may be an analysis chart indicating basis statistical amounts of a measurement result in a set section, and for example, may be basis statistical amounts of a measurement result based on an analysis result with respect to OCT data which becomes a basis of the motion contrast data.

The image data may be at least overlapped with the motion contrast data in relation to an acquiring part on the subject. For example, in relation to the acquiring part on the subject, the image data may be same as the motion contrast data. For example, in relation to the acquiring part on the subject, the image data may include the acquiring part of the motion contrast data.

Also, the analysis processing unit, for example, may perform the analysis process based on the changed analysis chart in association with a change of the analysis chart. Thus, a change with respect to analysis of the motion contrast in accordance with a setting change of the analysis chart can be smoothly performed.

For example, the analysis processing unit may change a position of the analysis region with respect to the motion contrast data in association with the change of a display position of the analysis chart. For example, the analysis processing unit may change a range of the analysis region with respect to the motion contrast data in association with the change of a range of the analysis chart.

In addition, for example, the analysis processing unit may change a reference position of the analysis process with respect to the motion contrast data in association with the change of the display position of the analysis chart.

The analysis processing unit may set, for example, a center position or a reference position of the analysis process with respect to the motion contrast data based on a center position of the analysis chart.

The analysis processing unit may perform a measurement process of the subject, for example, based on an analysis result from the analysis process.

The analysis processing unit may set the vascular channel analysis region based on the analysis chart. Also, the analysis processing unit may perform a vascular channel extraction process in the set vascular channel analysis region.

The analysis processing unit may perform measurement in relation to an extracted vascular channel. As the measurement in relation to the vascular channel, an region and a volume of the vascular channel, a density of the vascular channel, an amount of the vascular channel, a total amount of the vascular channel, a meandering degree of the vascular channel, a regularity of the vascular channel, a symmetry of the vascular channel, and the like may be used.

The analysis processing unit may set, for example, a reference position of a non-vascular channel extraction process in the motion contrast data based on a position of the analysis chart. Also, the analysis processing unit may perform the non-vascular channel extraction process based on the set reference position.

The apparatus may be further provided with, for example, a first instruction receiver (for example, controller 70). The first instruction receiver receives, for example, an instruction from an examiner for setting a position of the analysis chart on the image data. In this case, the analysis processing unit may perform the analysis process with respect to the motion contrast data based on the positional information of the analysis chart set by the first instruction receiver.

The image data may be at least one of, for example, a front image of the subject, an analysis map in relation to the subject, and the like.

The apparatus may be further provided with, for example, a second instruction receiver (for example, controller 70). The second instruction receiver receives, for example, an instruction from the examiner for setting a position of the analysis region or the reference position of the analysis process on the motion contrast data. In this case, the analysis processing unit may perform, for example, the analysis process with respect to the motion contrast data based on the positional information of the analysis region or the positional information of the reference position set by the second instruction receiver.

The analysis processing unit may set a position of the analysis chart based on the positional information of the analysis region or the positional information of the reference position set by the second instruction receiver.

The image data may be related to the OCT data which becomes a basis of the motion contrast data.

In a case in which extraction of the blood vessel region is performed by a threshold process as the analysis process, the analysis processing unit may set a region on the motion contrast data which is set for calculating a threshold based on the positional information of the analysis chart.

The apparatus may be provided with a third instruction receiver. The third instruction receiver receives, for example, an instruction from the examiner for selecting the analysis region in the motion contrast data. In this case, the analysis processing unit may set the analysis region on the image data based on the analysis region selected by the third instruction receiver.

The subject may be the fundus of the subject's eye. In this case, the analysis processing unit may be capable of respectively setting, for example, at least one of a position, range, and shape of the analysis region which are set for performing the analysis process according to an acquisition region on the subject of the motion contrast data. Of course, the position, range, shape, and the like of the analysis region may be respectively set, and the range may be changed according to the analysis result with respect to each data.

The acquisition region may be a surface direction of the subject (for example, macula, optic nerve head, and the like of fundus of subject's eye), and may be a depth direction of the subject (for example, in each layer of blood vessel, and the like of fundus of subject's eye).

In a case in which a plurality of the motion contrast data items having different acquisition regions are generated, a range of the analysis region may be respectively set in each data. The plurality of motion contrast data items may be, for example, a plurality of front surface motion contrast data items which is divided into each layer of blood vessel, and may be set the analysis region different in each front surface motion contrast data.

As the analysis map, for example, a map indicating a two-dimensional distribution of a measurement result in relation to the subject may be used. In this case, for example, a color map which is color-coded according to a measured value may be used.

For example, the analysis chart 504 may be an analysis chart for calculating basis statistical amounts of the measurement result of the subject in a preset section, and the basis statistical amounts inside the section may be measured.

EXAMPLE

Hereinafter, the OCT motion contrast data analysis apparatus of an example will be described with reference to drawings. The OCT motion contrast data analysis apparatus (hereinafter, OCT analysis apparatus) 1 illustrated in FIG. 1 performs an analysis process on the motion contrast data acquired by an OCT device 10.

The OCT analysis apparatus 1 is provided with, for example, the controller 70. The controller 70 is realized by, for example, a general CPU (central processing unit) 71, the flash ROM 72, a RAM 73, and the like. In the flash ROM 72, for example, an analysis process program for processing the motion contrast data, a program for obtaining the motion contrast data by controlling an operation of the OCT device 10, an initial value, and the like are stored. The RAM 73 temporally stores various information, for example.

In the controller 70, as illustrated in FIG. 1, for example, a storage unit (for example, non-volatile memory) 74, an operating unit 76, a display unit 75, and the like are electrically connected. The storage unit 74 is, for example, a non-transitory storage medium which is capable of holding storage contents even when power supply is blocked. For example, a hard disk drive, the flash ROM, a detachable USB memory, and the like can be used as the storage unit 74.

In the operating unit 76, various operation instructions by the examiner are input. The operating unit 76 outputs a signal in accordance with the input operation instruction to the CPU 71. In the operating unit 76, for example, a user interface of at least one of a mouse, a joystick, a keyboard, a touch panel, and the like may be used.

The display unit 75 may be a display which is mounted on a main body of the OCT analysis apparatus 1, and may be a display which is connected to the main body. For example, a display of a personal computer (hereinafter, refer to "PC") may be used. The display unit 75 displays, for example, the OCT data acquired by the OCT device 10, the motion contrast data, and the like.

For example, the OCT device 10 is connected to the OCT analysis apparatus 1 of the example. Also, the OCT analysis apparatus 1 may be integrally configured with a case same as, for example, the OCT device 10, or may be separately configured. The controller 70 may acquire the motion contrast data from the connected OCT device 10. The controller 70 may acquire the motion contrast data acquired by the OCT device 10 through a storage medium.

OCT Device

Figure 2:
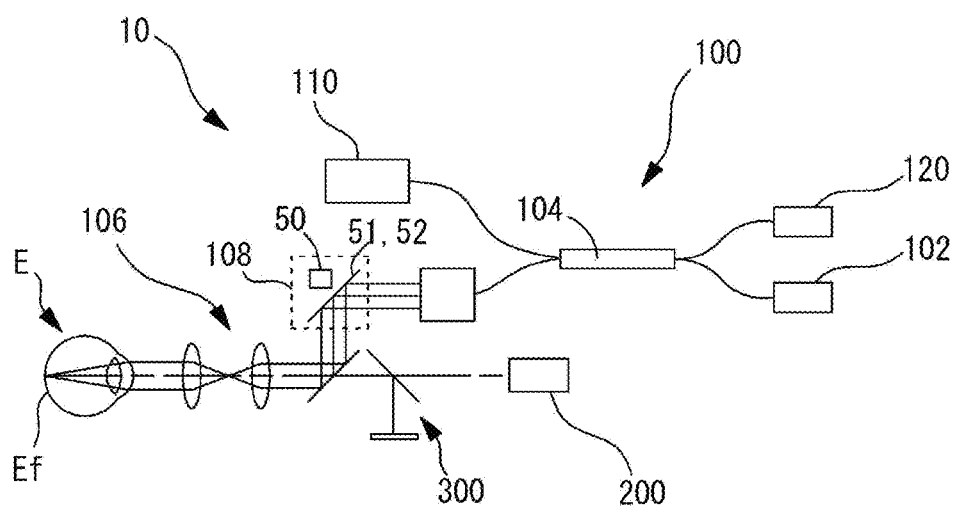
FIG. 2 is a view illustrating an example of an optical system of an OCT device.

Hereinafter, an outline of the OCT device 10 will be described on the basis of FIG. 2. For example, the OCT device 10 applies measuring light to a subject's eye E, and acquires an OCT signal acquired by reflecting light and the measuring light. The OCT device 10 is mainly provided with, for example, an OCT optical system 100.

OCT Optical System

The OCT optical system 100 applies the measuring light to the subject's eye E, and detects an interference signal of the reflecting light and reference light. The OCT optical system 100 is mainly provided with, for example, a measuring light source 102, a coupler (optical splitter) 104, a measurement optical system 106, a reference optical system 110, a detector 120, and the like. Also, regarding a detailed configuration of the OCT optical system, for example, refer to JP-A-2015-131107.

The OCT optical system 100 is an optical system of a so called optical coherence tomography (OCT). The OCT optical system 100 divides light emitted from the measuring light source 102 into the measuring light (sample light) and the reference light by the coupler 104. The measuring light is guided to the measurement optical system 106, and the reference light is guided to the reference optical system 110. The measuring light is guided to an fundus Ef of the subject's eye E through the measurement optical system 106. After that, the detector 120 receives the interference light by combining the measuring light reflected by the subject's eye E and the reference light.

The measurement optical system 106 is provided with, for example, a scanning unit (for example, light scanner) 108. The scanning unit 108 may be provided, for example, for scanning the measuring light in an XY direction on the fundus (transverse direction). For example, the CPU 71 controls an operation of the scanning unit 108 based on a scan position information which is set, and acquires the OCT signal based on a light receiving signal detected by the detector 120. The reference optical system 110 generates the reference light which is combined with a reflecting light acquired by reflection of the measuring light in the fundus Ef. The reference optical system 110 may be Michelson type or Mach-Zehnder type.

The detector 120 detects a interference state of the measuring light and the reference light. In a case of Fourier domain OCT, a spectral intensity of the interference light is detected by the detector 120, and a depth profile (A scan signal) in a predetermined range by Fourier transform with respect to spectral intensity data is acquired.

As the OCT device 10, for example, Spectral-domain OCT (SD-OCT), Swept-source OCT (SS-OCT), Time-domain OCT (TD-OCT), and the like may be used.

Front Imaging Optical System

The front imaging optical system 200 images, for example, the fundus Ef of the subject's eye E in a front direction (for example, optical axis direction of measuring light), and obtains a front image of the fundus Ef. The front imaging optical system 200 may be, for example, an apparatus configuration of a scanning type laser ophthalmoscope (SLO) (for example, refer to JP-A-2015-66242), and may be a so called fundus camera type configuration (refer to JP-A-2011-10944). Also, as the front imaging optical system 200, the OCT optical system 100 may be also used with, and the front image may be acquired on the basis of a detecting signal from the detector 120.

Fixation Target Projecting Unit

A fixation target projecting unit 300 includes the optical system for guiding a gaze direction of an eye E. The fixation target projecting unit 300 includes a fixation target being presented on the eye E, and is capable of guiding the eye E. For example, the fixation target projecting unit 300 has a visible light source which emits visible light, and changes a presentation position of the fixation target in two-dimension. Thus, the gaze direction is changed, and consequently, an acquiring part of the OCT data is changed.

Acquisition of Motion Contrast Data

Figure 3A:
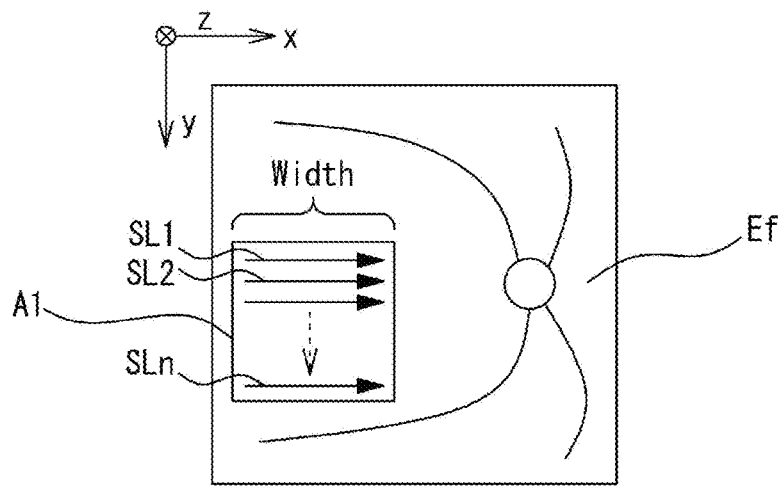
FIGS. 3A to 3C are views for describing acquisition of motion contrast.

The OCT analysis apparatus 1 of the example may acquire the motion contrast data, for example, by processing the OCT data detected by the OCT device 10. The CPU 71 controls driving of the scanning unit 108, and applies the measuring light to a region A1 on the fundus Ef. Also, in FIG. 3A, a direction of a z axis is set to a direction of an optical axis of the measuring light. A direction of an x axis is set to a horizontal direction of an examinee perpendicular to the z axis. A direction of an y axis is set to a vertical direction of the examinee perpendicular to the z axis.

For example, the CPU 71 applies the measuring light in an x direction along scan lines SL1, SL2, . . . , and SLn in a region A1. Also, scanning in a direction intersecting with an optical direction of the measuring light (for example, x direction) with the measuring light is referred to as "B scan". Two-dimensional OCT data obtained by one time B scan will be described as two-dimensional OCT data of one frame. The CPU 71 may obtain an A scan signal of a z direction in each scanning position by applying the measuring light to, for example, an xy direction in two-dimension.

The CPU 71 may acquire the motion contrast data based on the OCT data. The motion contrast may be, for example, information capturing a blood flow of the subject's eye, a change of a retinal tissue, and the like. In a case of acquiring the motion contrast data, the CPU 71 acquires at least two OCT data of the subject's eye in relation to a same position at different timings. For example, in each the scan line, the CPU 71 performs the B scan in multiple times at different timings, and respectively acquires a plurality of the OCT data items at different timings.

Figure 3B:
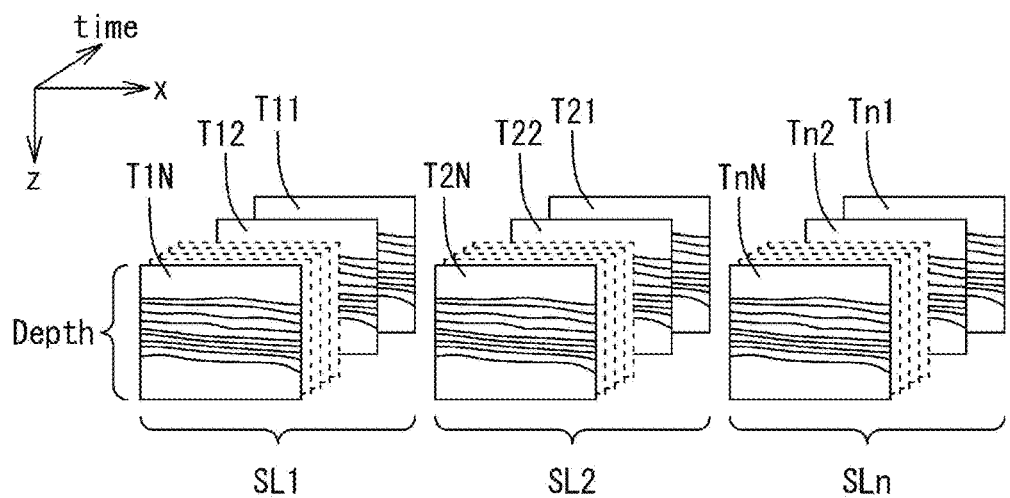
Figure 3C:
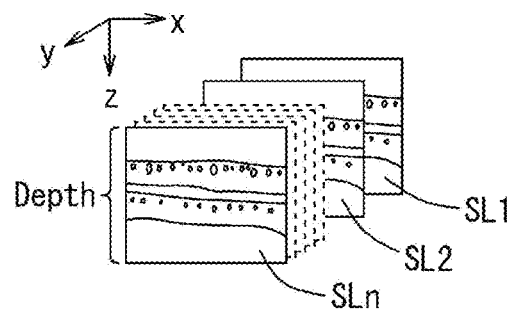

For example, FIG. 3B illustrates the OCT signal acquired in a case in which the B scan is performed in multiple times at different timings in the scan lines SL1, SL2, . . . , and SLn. For example, FIG. 3B illustrates a case of applying the scan line SL1 at timings T11, T12, . . . , and T1N, applying the scan line SL2 at timing T21, T22, . . . , and T2N, and applying the scan line SLn at timings Tn1, Tn2, . . . , and TnN. For example, the CPU 71 acquires the plurality of OCT data items at different timings in each the scan line, and stores the OCT data to the storage unit 74.

As described above, if the plurality of OCT data items in relation to the same position at the different timings are acquired, the CPU 71 acquires the motion contrast data by processing the OCT data. As a calculating method of the OCT data for acquiring the motion contrast, for example, a method of calculating an intensity difference of complex OCT data, a method of calculating a phase difference of the complex OCT data, a method of calculating a vector difference of the complex OCT data, a method of multiplying the phase difference and the vector difference of a complex OCT signal, a method of using a correlation of the signal (correlation mapping), and the like are exemplified. Also, as an example of a calculating manner, for example, refer to JP-A-2015-131107.

The CPU 71 may acquire three-dimensional motion contrast data of the subject's eye E by arranging the motion contrast data in different scan lines. Also, as described above, as the motion contrast data, the intensity difference, the vector difference, and the like may be acquired without being limited to the phase difference.

Analysis Process of Motion Contrast Data

An example of an analysis process of the motion contrast data acquired as described above will be described as follows.

The CPU 71 sets the analysis region with respect to the motion contrast data, and may acquire at least one analysis result by performing the analysis process in relation to the set analysis region. In this case, the CPU 71 may set the analysis region in the motion contrast data based on the positional information of the analysis chart on the image data different from the motion contrast data.

Hereinafter, as an example of the analysis result, a case, in which the blood vessel region of the subject's eye is extracted by the analysis process with respect to the motion contrast data, will be described. In this case, a blood vessel analysis region is set as the analysis region with respect to the motion contrast data, and the analysis process for extracting the blood vessel region at least in the blood vessel analysis region is performed.

Figure 4:
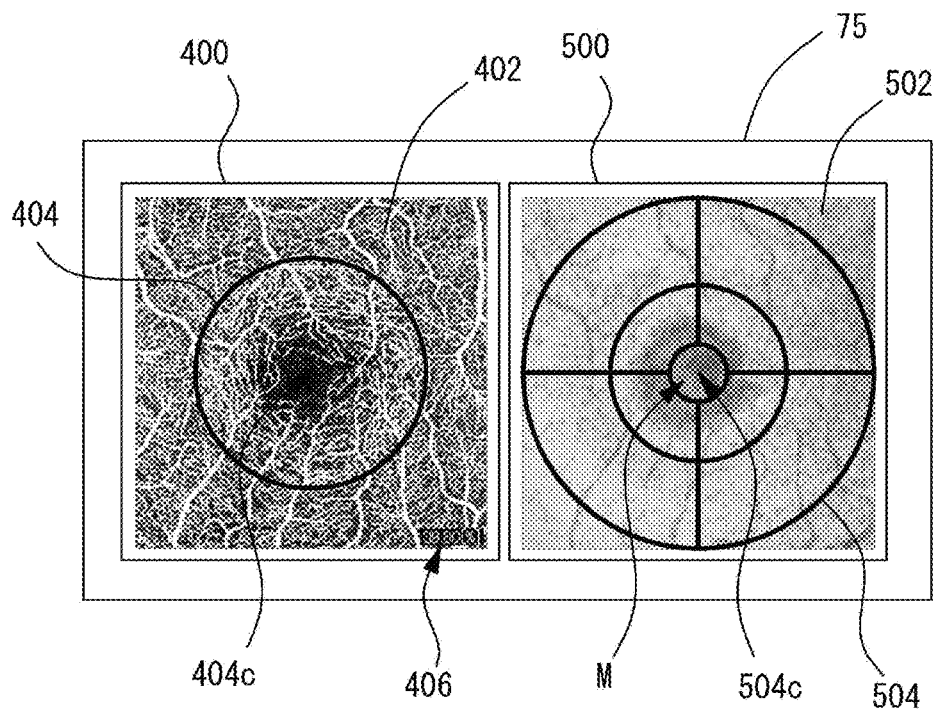
FIG. 4 is a view illustrating an example of a display screen.

FIG. 4 is a view illustrating an example of an example of an analysis screen at the time of extracting the blood vessel region. In the analysis screen, the CPU 71 may display, for example, an MC displaying region 400, a second image displaying region 500 on a display screen of the display unit 75. In this case, the MC displaying region 400 and the second image displaying region 500 may be displayed at the same time, and may be displayed at a different timing.

The MC displaying region 400 is a region for displaying the motion contrast data (hereinafter, MC data) 402, and for example, as the MC data 402, as illustrated in FIG. 4, front MC data (so called en face MC data) may be displayed. The front MC data may be acquired by, for example, taking out the three-dimensional MC data in relation to at least a part of region of a depth direction (for example, refer to Japanese Patent Application No. 2015-121574). For example, the front MC data may be generated by an integrated value or the maximum value in a depth direction in the MC data. Of course, as the MC data 402, one-dimensional MC data, two-dimensional MC data, and three-dimensional MC data may be displayed.

The CPU 71 may display a display (for example, graphic 404) indicating the blood vessel analysis region on the MC data 402 on the MC data 402. The display indicating the blood vessel analysis region may be a frame display indicating peripherals of the blood vessel analysis region as the graphic 404 of FIG. 4, and the blood vessel analysis region and a non-blood vessel analysis region may be displayed as a color-coded display.

The second image displaying region 500 is a region for displaying an image data 502 which is image data different from the MC data 402, and for example, at least any one of the front image and the analysis map may be displayed. As the image data 502, in relation to the acquiring part, the image data at least a part overlapping with the MC data 402 is used. For example, in a case in which the MC data 402 is data in which a macula part is set to a center, the image data in relation to macula is displayed, and in a case the MC data 402 is data in which an optic nerve head part is set to a center, the image data in relation to the optic nerve head may be displayed.

As the analysis map, for example, a map indicating two-dimensional distribution of the measurement result in relation to the fundus may be used. In this case, for example, color-coded color map according to a measured value may be used. As the analysis map, for example, a thickness map indicating a layer thickness, a comparison map indicating a compared result of the layer thickness of the subject's eye and a layer thickness of a normal eye stored in normal eye database, a deviation map indicating a difference between the layer thickness of the subject's eye and a layer thickness of a normal eye stored in a normal eye database in a standard deviation, and an examination date comparison thickness difference map indicating each examination date and a difference of thickness may be used. Also, in a case of calculating the layer thickness, for example, the OCT data is divide-processed in every layer by an image process (for example, segmentation process) with respect to the OCT data, and a thickness of each layer is measured based on an interval of a layer boundary. Of course, it is not limited to the layer thickness, as the analysis map, for example, a map indicating a curvature distribution of the fundus may be used.

The front image may be, for example, a front image imaged by the front imaging optical system 200, and may be the front OCT data (so called en face OCT data) generated from three-dimensional OCT data. In a case of the three-dimensional OCT data, it may be three-dimensional OCT data which becomes a basis of the three-dimensional motion contrast data. The analysis map may be a color map which realizes, for example, the analysis result (for example, thickness, curvature, and the like of fundus layer) on the subject's eye in two-dimension. In FIG. 4, as the image data 502, an image in which the analysis map is overlapped with the front image is illustrated.

Analysis Chart

The CPU 71 may display the analysis chart 504 so as to be overlap with the image data 502. In this case, the image data 502 may be associated with the measurement result (for example, measurement data of analysis map) in advance (registration) based on the analysis result with respect to the three-dimensional OCT data, and the measurement result corresponding to a region where the analysis chart 504 is set is output. In this case, the image data 502 is associated with the three-dimensional OCT data, the analysis process may be performed on a region where the analysis chart is set, and the measurement result may be output based on the analysis result. In this case, it is preferable that the three-dimensional OCT data is three-dimensional OCT data which becomes a basis of the MC data. This is because that positional correspondence (registration) between the MC data and the image data is easy and accurate.

For example, the analysis chart 504 may be an analysis chart for measuring the basis statistical amounts of the measurement result in a preset section, and the basis statistical amounts in the section may be measured. The section forming the analysis chart 504 may be one region or may be the plurality of sections. In a case of the plurality of sections, the basis statistical amounts in each divided section may be measured. As the basis statistical amounts, a representative value (average value, intermediate value, most frequent value, maximum value, minimum value, and the like), a scattering degree (distribution, standard deviation, variation coefficient), and the like may be used.

For example, the analysis chart 504 may be a chart which calculates an average in each region with respect to two-dimensional distribution of the layer thickness of the fundus. In addition, in the analysis chart 504, a numerical displaying region displaying the layer thickness in a predetermined region by a numerical value may be given. Instead of numerical displaying, in section unit, a color coding in accordance with the measurement result may be performed. Layer thickness data may be a sum of each layer, and may be a thickness of a certain layer (for example, optic nerve fiber layer).

The analysis chart 504 can be arbitrary selected, and in a case in which the thickness map is a macula map, as the analysis chart 504, for example, the examiner can select from a GCHART, a S/I chart, and an ETDRS. Also, in a case in which the thickness map is an fundus optic nerve head map, as the analysis chart, for example, the examiner can select from the entire charts, an up and down chart (divided into two), a TSNIT chart (divided into four), and a Clock-Hour chart (divided into twelve).

The CPU 71 receives an operation signal from the operating unit 76, and may change the display position of the analysis chart 504 on the image data 502. Thus, the analysis region is changed by the analysis chart 504 on the image data 502. The CPU 71 is associated with the change of the display position of the analysis chart 504, and the analysis result in the analysis region after being changed may be calculated. Also, a part of the analysis chart may be deviated from the image data 502.

For example, the examiner may set a center 504*c* of the analysis chart to a reference part (for example, central fovea center (refer to M in FIG. 4) of the fundus, optic nerve head center of nerve of eye, and abnormal part) by moving the analysis chart 504 using the operating unit 76. Thus, for example, when the reference part of the fundus is set as a center, the measurement result is obtained by the analysis chart 504. For example, the entire average layer thickness inside a chart in which the reference part is set as a center, the layer thickness of the reference part, an average layer thickness (for example, 1 mm, 2 mm, and 3 mm) inside a predetermined region in which the reference part is set as a center, and the like. Thus, a measurement result in which the reference part on the fundus is set as a center is obtained, and it is also clinically useful.

Association of Analysis Chart and Blood Vessel Analysis Region

For example, the CPU 71 may extract the blood vessel region on the MC data using the positional information of the analysis chart 504. More specifically, the CPU 71 may move a position of the blood vessel analysis region on the MC data in association with movement of the analysis chart 504. In this case, the CPU 71 may move a display (for example, graphic 404) indicating the blood vessel analysis region on the MC data 402. That is, in association with the movement of the analysis region by the analysis chart 504, a position of the blood vessel analysis region is changed.

As a result of the movement of the blood vessel analysis region, the blood vessel analysis region on the MC data is changed. Here, the CPU 71 may calculate the analysis result in the blood vessel analysis region after being changed, in association with the change of the blood vessel analysis region (a method of analyzing the blood vessel will be described later).

In a case in which the analysis chart and the blood vessel analysis region are associated with each other, the CPU 71 may move the blood vessel analysis region so that the center 504*c* of the analysis chart 504 in the image data 502 and a center 404*c* of the blood vessel analysis region in the MC data 402 are arranged at the same position in terms of analysis. That is, in the MC data 402, the CPU 71 may set the center of the analysis region to a position corresponding to the center position of the analysis chart 504 in the image data 502. In this case, it is preferable that the image data 502 and the MC data 402 are positionally associated with each other (registration).

Here, for example, in a case in which the examiner sets the center 504*c* of the analysis chart 504 to the reference part (for example, central fovea center, optic nerve head center of nerve of eye, and abnormal part) of the fundus, the center of the blood vessel analysis region is automatically set to be the reference part of the fundus. Thus, even when the analysis region is not changed on the MC data 402 again, the reference position of analysis can be coincide with an analysis by the analysis chart 504 and an analysis by the MC data 402.

Setting Blood Vessel Analysis Region

The blood vessel analysis region may be arbitrary set by the examiner. For example, the CPU 71 receives an operation signal from the operating unit 76, and may change a position of the blood vessel analysis region on the MC data. In this case, a position of a display indicating the blood vessel analysis region may be changed. The CPU 71 may calculate the analysis result in the blood vessel analysis region after being changed according to a change of the blood vessel analysis region. In this case, the CPU 71 may move the position of the analysis chart 504 on the image data 502 in association with the movement of the blood vessel analysis region. As a result, time and effort of position adjustment of the analysis chart 504 can be omitted.

In a case in which the plurality of motion contrast data items are analyzed, in association with the change of a position of the blood vessel analysis region in first motion contrast data, it may used to set a position of the blood vessel analysis region in second motion contrast data. For example, in relation to a depth direction of the fundus, it can be applied to analysis of a plurality of different motion contrast data items. In addition, the CPU 71 may remove an artifact in a second data region positionally corresponding to the first data region in the second motion contrast data using a first data region set on the first motion contrast data (for example, luminance of each pixel of the first data region is subtract from luminance of each pixel of second data region).

A range (size) of the blood vessel analysis region may be set by the examiner. The range of the blood vessel analysis region may be set according to the acquisition region of the MC data 402 on the fundus. The acquisition region may be set according to a different acquisition region in relation to a surface direction of the fundus. For example, in relation to macula part and optic nerve head part, a range may be respectively set.

Setting according to the acquisition region may be performed according to a different acquisition region in relation to the depth direction of the fundus. For example, in relation to a layer of a different blood vessel, the range may be respectively set. Of course, it is not limited to the layer of blood vessel, in relation to a different retinal layer (or choroid layer), the range may be respectively set. Thus, the blood vessel can be analyzed according to the acquisition region on the fundus. In a case in which the front MC data is generated in multiple in each the layer of blood vessel, the range of the blood vessel analysis region may be respectively set in advance in the front MC data of each layer of blood vessel. Thus, the blood vessel can be analyzed in accordance with each layer of blood vessel.

Figure 5:
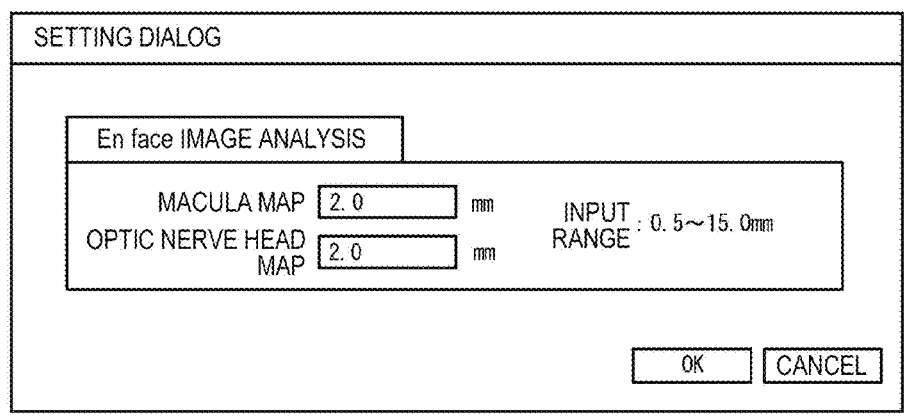
FIG. 5 is a view illustrating an example of a setting screen.

FIG. 5 is an example of the setting screen, a macula map indicates motion contrast data based on the macula, an optic nerve head map indicates motion contrast data based on the optic nerve head, and a range (for example, diameter) is set in map unit. Also, in a case of setting the range, for example, the CPU 71 may change a range (size) of the graphic 404 by receiving an operation signal from the operating unit 76. In addition, the range of the blood vessel analysis region may be same as a range of the analysis chart 504. In addition, based on the analysis chart 504, the range of the blood vessel analysis region may be set.

Also, in the above description, as a change parameter of the blood vessel analysis region, the position and range (size) of the blood vessel analysis region can be set, but it is not limited thereto. For example, a shape of the blood vessel analysis region may be set (for example, circle, ellipse, rectangle, or the like). In this case, according to the acquisition region of the MC data 402 on the fundus, the shape of the blood vessel analysis region may be set.

The blood vessel analysis region may be a region which is divided into the plurality of sections, and the blood vessel analysis in each section may be performed. A plurality of the blood vessel analysis regions in which any one of an arranged position and a range (size) of each section is different may be selected.

In this case, according to the acquisition region of the MC data 402 on the fundus, a division pattern of the blood vessel analysis region may be set. For example, a superficial capillary plexus may be the entire chart (one section), and an intermediate capillary plexus may be a S/I chart (section divided into two of up and down). In this case, the arranged position and range of each section of the blood vessel analysis region may be set to be same as a arranged position and a range of each section of the analysis chart 504. Thus, the analysis result of each section of the analysis chart 504 and the analysis result of each section in the blood vessel analysis region can be evaluated in association with each other. Accordingly, a relativity between a blood vessel analysis result of the fundus and a shape the analysis result (for example, layer thickness) of the fundus can be check in section unit.

Blood Vessel Extraction Process and Blood Vessel Measurement

The CPU 71 may display the measurement result in the set blood vessel analysis region on the display unit 75 by analyzing the MC data 402 in the blood vessel analysis region set as described above. Consequently, measurement in the analysis chart and measurement with respect to the MC data 402 are can be smoothly performed. Also, the analysis result may be displayed, for example, as a numerical value 406 on the MC displaying region 400.

For example, the CPU 71 performs a determination process of the blood vessel region and the non-blood vessel region by performing analysis due to an image process set as the blood vessel analysis region on the MC data. The blood vessel region is extracted by the determination process. In this case, the non-blood vessel region may be extracted by the determination process.

The determination process may be, for example, a threshold process, a pixel satisfying a threshold may be determined as the blood vessel region, and a pixel not satisfying the threshold may be determined as the non-blood vessel region. The threshold itself may be arbitrarily set by the examiner, and may be set in advance as a fixing value. In addition, the threshold may be set through a pixel analysis process with respect to the MC data 402.

For example, the CPU 71 may perform measurement with respect to the blood vessel region based on a result of the determination process. The CPU 71 may measure the blood vessel region based on the blood vessel region extracted by the determination process. The measurement result may be, for example, a blood vessel density and a blood vessel region. As the density of the blood vessel region, for example, the blood vessel region (amount of blood vessel) per unit region is calculated by calculating a ratio of the blood vessel region in the entire blood vessel analysis region. As the measurement result, it is not limited thereto, for example, a total amount of the blood vessels, a meandering degree of the blood vessel, a regularity of the blood vessel, and the like may be used. Also, in a case in which the blood vessel analysis region is divided into the plurality of sections, the CPU 71 may calculate a ratio and a different of the measurement result between each section. Thus, for example, a symmetry, and the like of the blood vessel can be calculated.

Relating to blood vessel measurement, there is a case in which a scanning range of OCT according to an axial length of eye is different, and thus the CPU 71 may correct the measurement result according to a value of the axial length of eye of the subject's eye. Also, the CPU 71 may determine and display the blood vessel region and the non-blood vessel region based on a result of the determination process, and for example, may display the blood vessel region in color.

For example, the CPU 71 perform re-analysis according to a change of the blood vessel analysis region, and may update the result of the blood vessel extraction process. In this case, the CPU 71 may update the result of the blood vessel extraction process, and update the measurement result in relation to the blood vessel region based on the updated result of blood vessel extraction.

For example, the CPU 71 may update the measurement result in relation to the blood vessel region according to the change of the blood vessel analysis region in association with the change of the analysis chart 504. Thus, in a case in which the examiner sets the center 504*c* of the analysis chart 504 to the reference part (for example, central fovea center and optic nerve head center of nerve of eye) of the fundus, blood vessel measurement in which the reference part of the fundus is set to the center can be smoothly performed.

In a case in which the determination process of the blood vessel region and the non-blood vessel region is automatically performed, the CPU 71 may determine the blood vessel and the non-blood vessel regions by applying a binarization process (for example, determining analysis method) from a luminance value of the MC data 402. In a case in which the analysis chart 504 includes the plurality of sections, a threshold in a region unit corresponding to each section of the chart may be set, and a threshold in the entire region corresponding to the entire chart may be set. In addition, in a case in which the blood vessel analysis region is divided into the plurality of sections, the threshold in a region unit corresponding to each section may be set, and the threshold in the entire blood vessel analysis region may be set.

In this case, when only a predetermined region (for example, 2.0 mm) from a center coordination corresponding to the center 504*c* of the analysis chart 504 is set to a target region at the time of calculating a binarization parameter (threshold), the CPU 71 may perform the binarization process with respect to a vicinity region further than the object region using the calculated parameter.

A peripheral part of the MC data 402 frequently includes unnecessary components. For example, in a case in which the axial length of eye is long, or the like, a curvature of the eye is great, and thus if imaging is performed at an angle having a wide range, there is no OCT data itself which becomes a basis. In addition, there is a case in which the eye is moved to an end part of the data (for example, side where imaging is end), and the OCT data which becomes a basis is widen. Here, the determination process can be accurately performed by using a position of the analysis chart 504.

Detection of Central Fovea Non-Blood Vessel Region (FAZ) using Analysis Chart

Next, a case of extracting a FAZ of the subject's eye by the analysis process with respect to the MC data 402 will be described. In this case, the analysis process for extracting a non blood vessel analysis region is performed with respect to the MC data.

Figure 6:
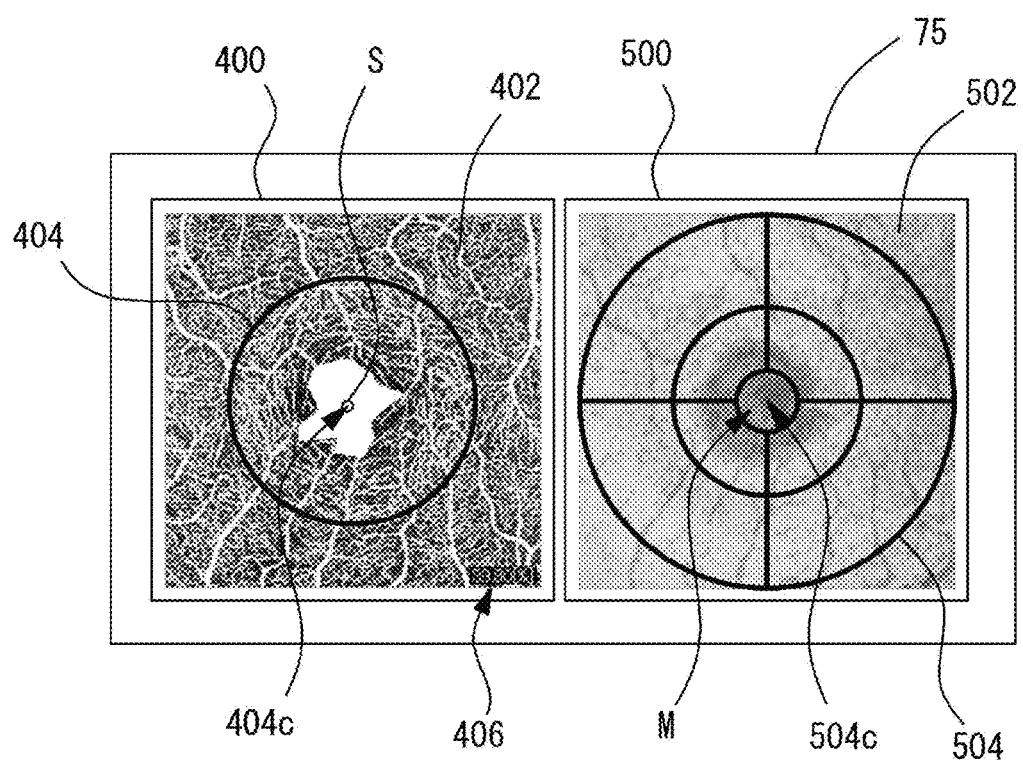
FIG. 6 is a view illustrating an example of the display screen.

FIG. 6 is a view illustrating an example of an analysis screen at the time of extracting the FAZ. Also, components given the same numeral as that of FIG. 4 have the same functions and configurations as long as there is no specific description.

For example, the CPU 71 may perform the extraction process of the central fovea non-blood vessel region (hereinafter, FAZ) on the MC data using the positional information of the center 504*c* of the analysis chart 504. More specifically, in a case of extracting the FAZ by an image process, the CPU 71 may extract a region corresponding to the FAZ by analyzing a pixel value of a vicinity based on a seed point S (start of region detection).

Since the FAZ has a low luminance value in the non-blood vessel region, for example, the FAZ is extracted by determining connectedness with luminance of a peripheral of the center part based on the seed point S set in a center part of the FAZ. Also, as a manner of the extraction process, for example, in addition to the extraction process based on a graph theory, there are extraction by region expansion method, and extraction by a dynamic contour model like Snake and Level Set. In addition, a manner disclosed in "Noninvasive Imaging of the Foveal Avascular zone with High-Speed, Phase-Variance Optical Coherence Tomography" by Kim et al, January, 2012 may be used.

Here, the CPU 71 may set the reference position of a non-blood vessel extraction process so that the center 504*c* of the analysis chart 504 in the image data 502 and the reference position (for example, seed point S) of the analysis process on the MC data 402 are arranged on the same position in terms of analysis. Here, the CPU 71 allows a position of the center 504*c* of the analysis chart 504 to be coincide with the reference position (for example, the seed point S) of the non-blood vessel extraction process on the MC data 402. That is, in the MC data 402, the CPU 71 may set the reference position of the analysis process on a position corresponding to the center position the analysis chart 504 in the image data 502. In this case, it is preferable that the image data 502 and the MC data 402 are positionally related to each other (registration).

For example, in a case in which the center 504*c* of the analysis chart 504 is set in the central fovea center, the reference position of the analysis process (for example, position of seed point S) is set in the central fovea center, and thus the FAZ can be smoothly detected. If the position is deviated from the reference position of the analysis process, there is a possibility that the image process is performed based on the blood vessel region, and a possibility that the FAZ extraction accuracy is lowered.

Of course, the CPU 71 may set the reference position in the analysis process, and may detect the FAZ based on the set reference position by the image process when receiving the operation signal from the operating unit 76. In this case, the CPU 71 may change the display position of the analysis chart 504 so that the reference position of the analysis process at the time of extracting the FAZ and the center 504*c* of the analysis chart 504 are arranged on the same position in terms of analysis.

The above analysis is not limited to the blood vessel, and can be applied to a vascular channel analysis (for example, a lymphatic vessel) as the vascular channel analysis region.

In the above description, the analysis process limited to the analysis region is performed, but is not limited thereto, and the CPU 71 may perform the analysis process with respect to the set analysis region and may also perform the analysis process with respect to another region.

In the above description, the front MC data was described as an example, but the MC data can be applied to the embodiment. For example, the analysis region of the three-dimensional MC data may be set on the three-dimensional OCT data based on the positional information of the analysis chart. Of course, as the MC data, for example, one-dimensional MC data and two-dimensional MC data may be used.

In the above description, the measurement result of the blood vessel with respect to the MC data is output on the MC data which is displayed on the display unit 75, but it is not limited thereto, and only the measurement result performed by the CPU 71 may be displayed with the image data 502 without displaying the MC data. Accordingly, a display on the screen can be simplified.

In the above description, as the image data, the front image of the subject and the analysis map related to the subject are used, but, for example, the second motion contrast data different from the motion contrast data performing the analysis process may be used. Thus, the analysis of the plurality of motion contrast data items can be smoothly.

In addition, in a case in which the MC data in wide range is generated by combining a plurality of different front MC data items in relation to a surface direction of the fundus, the CPU 71 may set a wider region than one front MC data to the analysis region. Accordingly, the analysis in a wide range can be performed. In addition, the CPU 71 may set the analysis region in each front MC data forming the MC data in the wide range generated as described above. In this case, a plurality of the analysis regions in each front MC data may be set.

In the above description, the fundus of the subject's eye was described as an example, but it is not limited thereto, and can be applied to even an anterior eye of the subject's eye. Further, it is not limited to the subject's eye, and can be applied for even another motion contrast data (for example, motion contrast data in a tissue other than eye) acquired by the OCT.

What is claimed is:

1. An OCT motion contrast data analysis apparatus comprising:
    a processor; and
    memory storing computer readable instructions, when executed by the processor, causing the OCT motion contrast data analysis apparatus to execute:
    acquiring OCT motion contrast data of a subject's eye by optical coherence tomography, wherein the OCT motion contrast data is fundus motion contrast image data of a blood vessel analysis region of the subject's eye; and
    performing an analysis process with respect to the OCT motion contrast data based on an analysis chart set on image data different from the OCT motion contrast data in an extraction of blood vessels in the blood vessel analysis region.

2. The OCT motion contrast data analysis apparatus according to claim 1, wherein the analysis process is associated with a change of the analysis chart and is performed based on the changed analysis chart.

3. The OCT motion contrast data analysis apparatus according to claim 1, wherein the analysis processor sets a center position or a reference position of the analysis process with respect to the OCT motion contrast data based on a center position of the analysis chart.

4. The OCT motion contrast data analysis apparatus according to claim 1, wherein the analysis processor performs a measurement process on the subject based on an analysis result from the analysis process.

5. The OCT motion contrast data analysis apparatus according to claim 1, wherein the analysis processor sets a vascular channel analysis region based on the analysis chart, and performs a vascular channel extraction process in the set vascular channel analysis region.

6. The OCT motion contrast data analysis apparatus according to claim 1, wherein the analysis processor sets a reference position of a non-vascular channel extraction process in the OCT motion contrast data based on a position of the analysis chart, and performs the non-vascular channel extraction process based on the set reference position.

7. The OCT motion contrast data analysis apparatus according to claim 1, wherein the computer readable instructions, when executed by the processor, cause the OCT motion contrast data analysis apparatus to function as:
    an instruction receiver configured to receive an instruction from an examiner for setting a position of the analysis chart on the image data;
    wherein the analysis process is performed with respect to the OCT motion contrast data based on positional information of the analysis chart set by the instruction receiver.

8. The OCT motion contrast data analysis apparatus according to claim 1, wherein the image data includes at least one of OCT data of the subject, a front image of the subject, and an analysis map related to the subject.

9. The OCT motion contrast data analysis apparatus according to claim 1, wherein the image data relates to OCT data which is to be a basis of the OCT motion contrast data.

10. The OCT motion contrast data analysis apparatus according to claim 1, wherein the image data is different from the OCT motion contrast data with which the analysis process is performed.

11. The OCT motion contrast data analysis apparatus according to claim 1, wherein the computer readable instructions, when executed by the processor, cause the OCT motion contrast data analysis apparatus to function as an instruction receiver configured to receive an instruction from an examiner for setting a position of an analysis region or a reference position of the analysis process on the OCT motion contrast data,
    wherein the analysis process is performed with respect to the OCT motion contrast data based on positional information of the analysis region or positional information of the reference position set by the instruction receiver.

12. The OCT motion contrast data analysis apparatus according to claim 1, wherein in a case of performing extraction of a blood vessel region by a threshold process, a region on the OCT motion contrast data set for calculating a threshold is set based on positional information of the analysis chart.

13. The OCT motion contrast data analysis apparatus according to claim 1, wherein the computer readable instructions, when executed by the processor, cause the OCT motion contrast data analysis apparatus to function as an instruction receiver configured to receive an instruction from an examiner for setting an analysis region on the OCT motion contrast data,
    wherein an analysis region on the image data is set based on the analysis region set by the instruction receiver.

14. The OCT motion contrast data analysis apparatus according to claim 1,
    wherein the subject is a fundus of the subject's eye, and
    wherein at least one of a position, a range, and a shape of an analysis region which are used for performing the analysis process is set according to an acquisition region on the subject of the OCT motion contrast data.

15. The OCT motion contrast data analysis apparatus according to claim 1,
    wherein the analysis chart is for measuring basis statistical amounts for measurement results of the subject in a plurality of sections which are preset.

16. The OCT motion contrast data analysis apparatus according to claim 1, wherein an analysis region which is set for performing the analysis process is set and divided into a plurality of sections on the OCT motion contrast data based on the analysis chart, and wherein a arranged position and a range of each of the plurality of sections of the analysis region are set to be the same as a arranged position and a range of each of a plurality of sections of the analysis chart.

17. The OCT motion contrast data analysis apparatus according to claim 16, wherein an analysis result of each of a plurality of sections in the analysis region and an analysis result of each a plurality of sections of the analysis chart are associated with each other and are evaluated.

18. An OCT motion contrast data analysis method comprising:

acquiring OCT motion contrast data of a subject's eye by an optical coherence tomography, wherein the OCT motion contrast data is fundus motion contrast image data of a blood vessel analysis region of the subject's eye; and performing an analysis process with respect to the OCT motion contrast data based on an analysis chart set on image data different from the OCT motion contrast data in an extraction of blood vessels in the blood vessel analysis region.

* * * * *